(12) United States Patent
Zahynacz et al.

(10) Patent No.: US 11,179,266 B2
(45) Date of Patent: Nov. 23, 2021

(54) SURGICAL HAND WRAP AND STERILE CONNECTOR

(71) Applicant: Smith & Nephew, Inc., Memphis, TN (US)

(72) Inventors: Daniel Zahynacz, Somerville, MA (US); William D. Obendorf, Chelmsford, MA (US); Graham Smith, Newburyport, MA (US); Scott Trenhaile, Memphis, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 317 days.

(21) Appl. No.: 16/181,432

(22) Filed: Nov. 6, 2018

(65) Prior Publication Data

US 2019/0133808 A1 May 9, 2019

Related U.S. Application Data

(60) Provisional application No. 62/582,989, filed on Nov. 8, 2017, provisional application No. 62/703,126, filed on Jul. 25, 2018.

(51) Int. Cl.
*A61F 5/37* (2006.01)
*A61L 31/06* (2006.01)
(Continued)

(52) U.S. Cl.
CPC .......... *A61F 5/3769* (2013.01); *A61B 17/025* (2013.01); *A61B 46/00* (2016.02);
(Continued)

(58) Field of Classification Search
CPC .... A61F 5/3796; A61F 5/0118; A61F 5/3761; A61F 5/37; A61F 5/01; A61F 5/05841;
(Continued)

(56) References Cited

U.S. PATENT DOCUMENTS 4,616,637 A * 10/1986 Caspari ............... A61F 5/04
5/623
5,003,967 A * 4/1991 McConnell ........... A61G 13/12
2/158

(Continued)

OTHER PUBLICATIONS

T. Richards et al., Acute hand injury splinting—the good, the bad and the ugly, Feb. 2018, (Year: 2018).*

*Primary Examiner* — Alireza Nia
*Assistant Examiner* — Daniel A Miller
(74) *Attorney, Agent, or Firm* — Burns & Levinson, LLP; Joseph M. Maraia; Marlo Schepper Grolnic

(57) ABSTRACT

Devices to secure the hand of a patient to a limb positioning device while evenly distributing the applied traction load across the patient's hand and wrist are disclosed. The hand is placed in the open position into a soft mitten, while an anatomically-shaped plate is attached to the mitten for supporting the palm of the hand in the open position. Straps are then secured around the patient's wrist and hand. Finally, the entire device is overwrapped an elastic bandage and secured to the limb positioning device. When traction is applied, the shape of the plate, the construction of the mitten, and the straps combine to allow low-contact pressure across the patient's hand and wrist.

12 Claims, 7 Drawing Sheets

(51) Int. Cl.
*A61L 31/04* (2006.01)
*A61L 31/14* (2006.01)
*A61B 46/20* (2016.01)
*A61B 46/23* (2016.01)
*A61F 5/01* (2006.01)
*A61B 46/00* (2016.01)
*A61B 17/02* (2006.01)
*A61B 46/10* (2016.01)
*A61B 46/27* (2016.01)
*A61G 13/12* (2006.01)
*A61G 13/00* (2006.01)

(52) U.S. Cl.
CPC ............. *A61B 46/10* (2016.02); *A61B 46/20* (2016.02); *A61B 46/23* (2016.02); *A61B 46/27* (2016.02); *A61F 5/0118* (2013.01); *A61F 5/3761* (2013.01); *A61G 13/124* (2013.01); *A61L 31/048* (2013.01); *A61L 31/049* (2013.01); *A61L 31/06* (2013.01); *A61L 31/146* (2013.01); *A61B 2046/201* (2016.02); *A61G 13/0045* (2016.11); *A61G 13/0072* (2016.11); *A61G 13/1235* (2013.01)

(58) Field of Classification Search
CPC .. A61F 5/0585; A61F 5/05866; A61F 5/3769; A61G 13/124; A61G 13/0072; A61G 13/0045; A61G 13/1235; A61G 13/00; A61G 13/12; A61G 13/129; A61G 13/08; A61G 13/101; A61L 31/06; A61L 31/049; A61L 31/146; A61L 31/048; A61B 46/20; A61B 46/10; A61B 46/27; A61B 46/23; A61B 46/00; A61B 2046/201; A61B 17/025; A61M 5/52; Y10T 403/7105; Y10T 403/7129; Y10T 403/7141; Y10T 403/7171; Y10T 403/7194
USPC ............................................ 602/21; 128/879
See application file for complete search history.

(56) References Cited

U.S. PATENT DOCUMENTS

| | | | |
|---|---|---|---|
| 5,069,203 A * | 12/1991 | Anderson | A61F 13/108 602/21 |
| 5,074,291 A * | 12/1991 | Carter | A61G 13/0045 606/241 |
| 5,156,168 A * | 10/1992 | Canterna | A61F 5/05866 128/879 |
| 5,419,756 A * | 5/1995 | McConnell | A61G 13/12 602/21 |
| 6,681,772 B2 * | 1/2004 | Atwater | A61F 5/3761 128/878 |
| 7,406,967 B2 * | 8/2008 | Callaway | A61M 5/52 128/877 |
| 2005/0177081 A1 * | 8/2005 | Scheinberg | A61F 5/0111 602/21 |
| 2009/0260638 A1 * | 10/2009 | Duplessie | A41D 19/01 128/879 |
| 2015/0150717 A1 * | 6/2015 | Lowe | A61H 1/008 601/151 |
| 2017/0013898 A1 * | 1/2017 | Lewis | A41D 19/01582 |
| 2018/0000624 A1 * | 1/2018 | Mason | A61F 5/058 |
| 2019/0350792 A1 * | 11/2019 | Catacchio | A61G 13/0072 |

* cited by examiner

SURGICAL HAND WRAP AND STERILE CONNECTOR

CROSS-REFERENCE TO RELATED APPLICATIONS

This application claims priority to and benefit of U.S. Provisional Application No. 62/582,989, filed Nov. 8, 2017, and U.S. Provisional Application No. 62/703,126, filed Jul. 25, 2018, both entitled SURGICAL HAND WRAP AND STERILE CONNECTOR, the contents of which are incorporated by reference herein in their entirety for all purposes.

FIELD

This disclosure relates generally to devices which are used to position a limb of a patient during a medical procedure and, more particularly, to devices which are used to position the shoulder and arm of a patient during shoulder surgery.

BACKGROUND

Orthopedic shoulder surgery involves complexities not encountered in other surgeries, such as knee surgery. For example, during shoulder surgery, ports or incisions are placed through a patient's shoulder joint in order to provide access for instruments such as light sources, visual scopes, and surgical tools. However, it is sometimes desirable for a surgeon to gain access to a different area of the joint, without creating new ports, by rotating the operative limb and holding it in a new position. This distraction is achieved by applying traction to the arm via the hand and/or the forearm while it is secured to a limb positioning device.

Traction loads of up to 30 lbs generally require that the hand be tightly secured to the limb positioning device. To accomplish this, the hand may be attached to a handle or bar and secured over the bar into a balled fist. The arm and hand are typically draped or covered in a sleeve and the entire arm is wrapped with an elasticated bandage. The distal end of the sleeve is then attached to the limb positioning device. However, this method of securing the hand can lead to numbness in the patient's hand and fingers, and furthermore reduces control of the rotation of the hand and wrist.

Another problem inherent to the use of limb positioning devices is that the non-sterile limb positioning device is usually clamped to the operating room table. A sterile connection is typically made to the patient by passing a sterile rope with a hook attached to its distal end through the limb positioning device, while the sleeve covering the patient's arm and hand is attached to the hook. However, this procedure requires a non-sterile operating assistant outside of the sterile field to pass the rope to a sterile operating assistant inside the sterile field, which leads to the possibility of cross-contamination.

BRIEF SUMMARY

Described herein is a device to secure the hand of a patient to a limb positioning device while evenly distributing the applied traction load across the patient's hand and wrist. The hand is placed in the open position into a soft mitten, while an anatomically-shaped plate is attached to the mitten, supporting the palm of the hand. Straps are then secured around the patient's wrist and hand. Finally, the entire device is overwrapped an elastic bandage and secured to the limb positioning device. When traction is applied, the shape of the plate, the construction of the mitten, and the straps advantageously combine to allow low-contact pressure across the patient's hand and wrist. Further described herein is a sterile drape with a sterile connector and its distal end, which advantageously allows a sterile operating assistant to connect and disconnect the surgical hand wrap of this disclosure from the limb positioning device. This in turn allows for faster turnover between procedures by eliminating the need for re-usable (i.e., autoclaveable) interfaces.

Further examples of the surgical hand wrap and sterile connector of this disclosure may include one or more of the following, in any suitable combination.

In examples, the surgical hand wrap of this disclosure includes a flexible mitten portion having an interior side and an exterior side. The mitten portion is configured to enclose at least a hand of the patient in an open position. The hand wrap also includes an anatomically-shaped plate for supporting a palm of the hand in the open position and at least one closeable strap for wrapping around the exterior side of the mitten portion. When traction is applied to the patient's arm, the plate, the mitten portion, and the at least one strap combine to allow low-contact pressure across the hand of the patient.

In further examples, the mitten portion is comprised of at least one of urethane foam and polyester fabric. In examples, the interior side of the mitten portion includes an anti-slip material, which may be one of SBR bonded foam, rubber, and urethane foam. In examples, an end of the at least one strap is attached to the mitten portion. In other examples, the at least one strap is free-floating. In further examples, the at least one strap is secured to the plate and the hand wrap is enclosed within a bandage. In examples, the plate is made of polycarbonate plate. In examples, the plate has a distal portion configured to attach to the limb positioning device and a curved center portion for supporting the palm of the hand in the open position. In examples, the plate includes at least one slot configured for the passage of the at least one strap. In further examples, a padding is disposed within the mitten portion for securing about a wrist of the patient. A thickness of the padding is selected to be greater than a thickness of the mitten portion.

In examples, the sterile connector of this disclosure includes a T-fitting at a distal end configured to couple to a support member of a sterile hand wrap and a shaft at a proximal end configured to mate with a receiver of the limb positioning device. The connector is attached to a flexible dam portion at a distal end of a sterile covering, the covering configured to cover at least a portion of the limb positioning device. In examples, the connector is made of polymers or metals. In examples, the covering is made of a clear, polyethylene plastic. In examples, the flexible dam portion is made of rubber. In examples, a proximal end of the covering is open to cover at least a portion of the limb positioning device. In examples, the covering is configured to fold in a telescopic fashion. In examples, the connector is attached to the flexible dam portion in an interference fit. In other examples, the connector is attached to the distal end of the covering.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
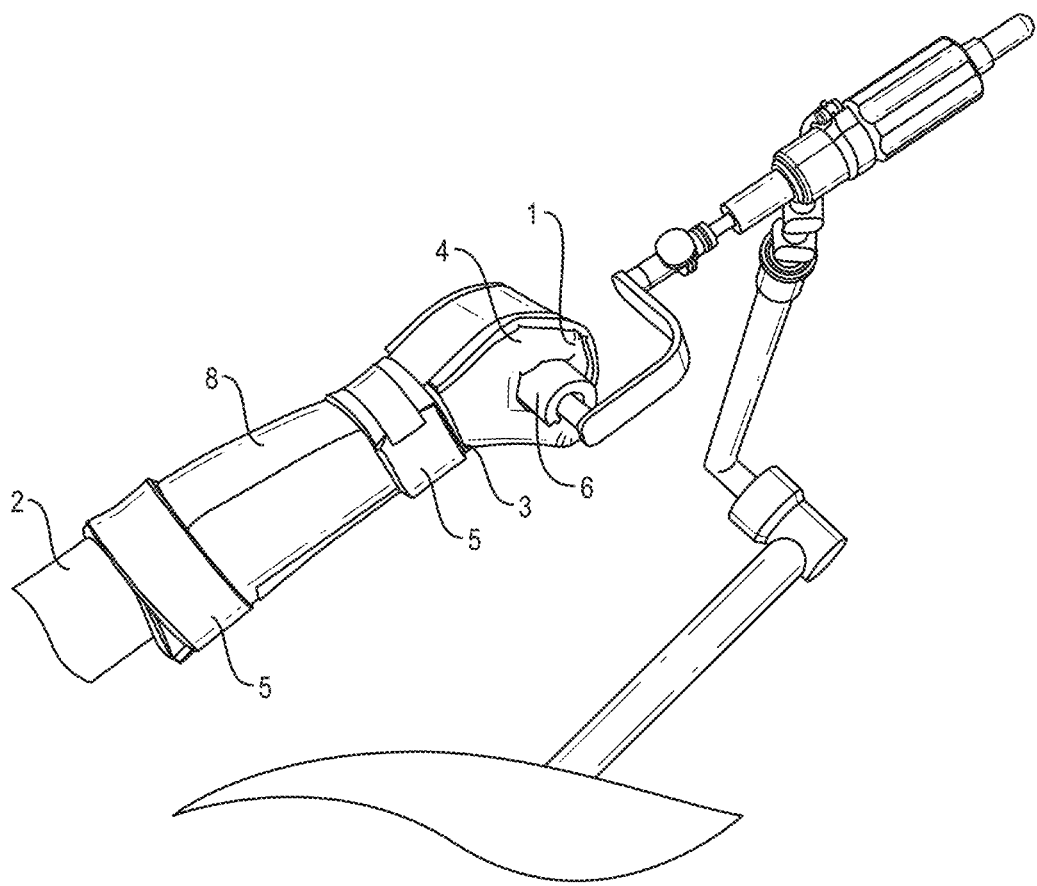
FIGS. 1A and 1B illustrate a prior art surgical hand wrap.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Figure 1B:
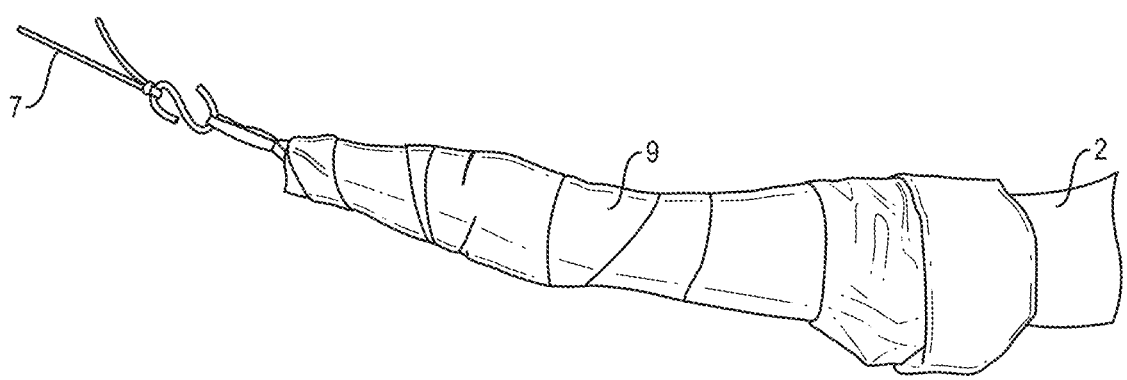
Figure 1C:
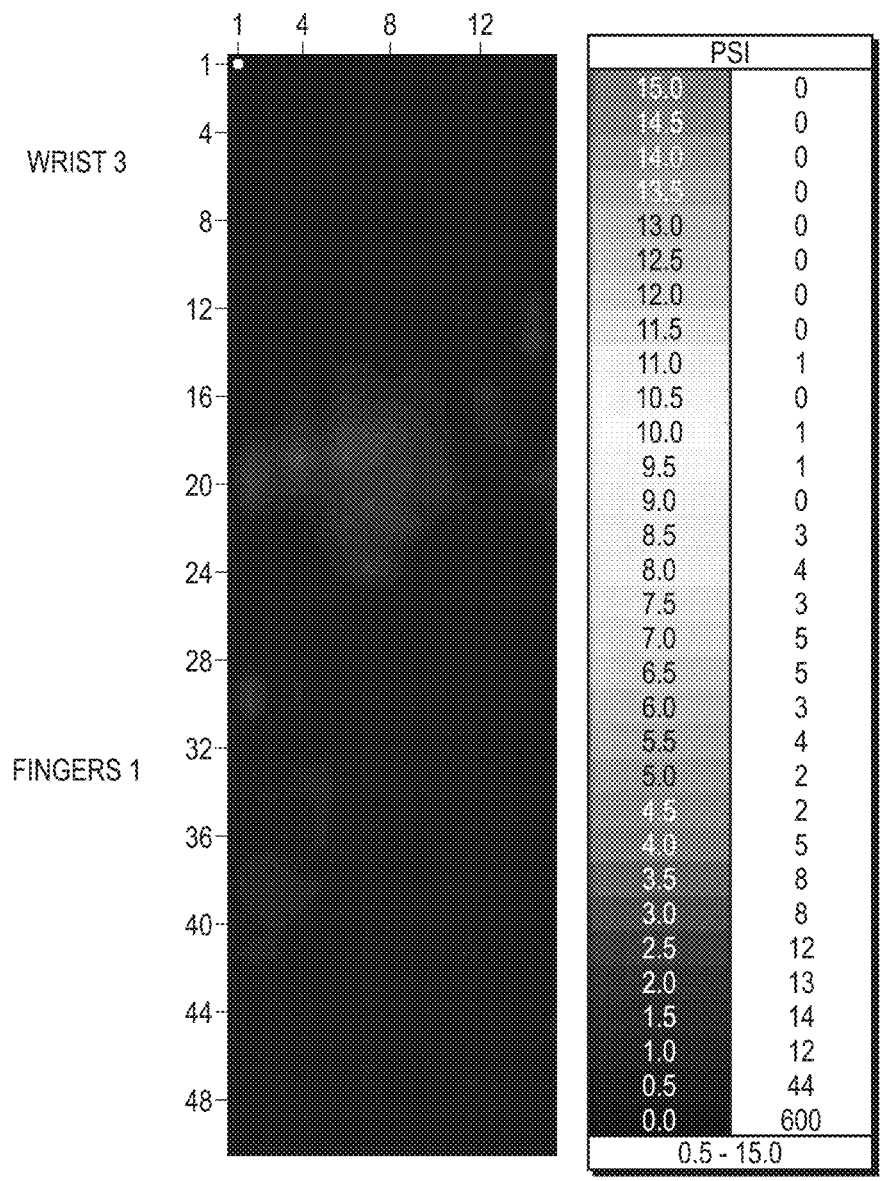
FIG. 1C shows the pressure distribution across the hand and wrist under a typical traction load.

FIGS. 1A and 1B illustrate a prior art surgical hand wrap for attaching a patient's arm 2 and hand 4 to a limb positioning device. Typically, before being secured to the limb positioning device, the patient's hand 4 is attached to a handle or bar 6 and secured into a balled fist, as shown in FIG. 1A. Portions of the arm 2 and the hand 4 are draped or covered in a flexible sleeve 8 and secured in place with straps 5. The entire arm 2 is then wrapped with an elasticated bandage 9, as shown in FIG. 1B. The distal end of the bandage 9 is attached to weights via a rope 7 and a series of pulleys on a limb positioning device, such as the limb positioning device illustrated in FIG. 5A. However, this method of securing the hand 4 can lead to numbness in the patient's hand 4 and fingers 1. FIG. 1C shows the high-contact pressure points across the fingers 1 and wrist 3 of the patient under traction load when the hand 4 and arm 2 are attached to the limb positioning device in this manner. Such high-contact pressure points can lead to the numbing effect of the hand 4 and fingers 1.

Figure 2:
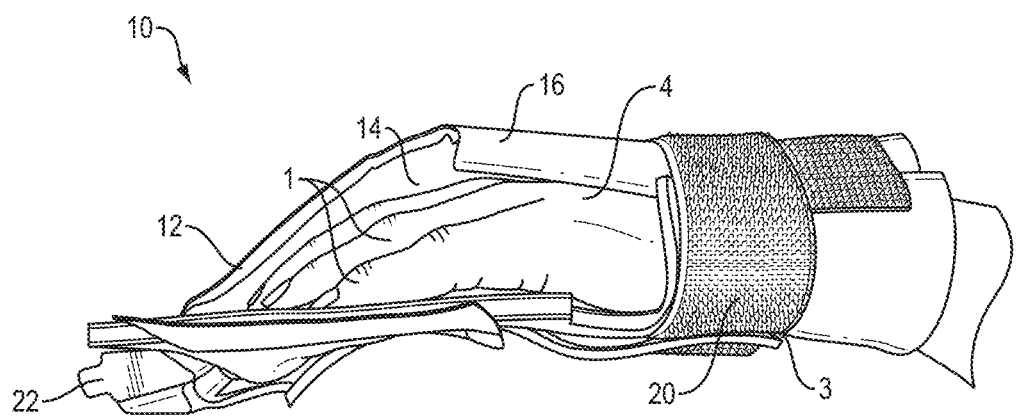
FIG. 2 is a cut-away view of an exemplary mitten portion of the hand wrap of this disclosure.

Turning now to FIG. 2, a cut-away view of an exemplary surgical hand wrap 10 of this disclosure is shown. As illustrated in FIG. 2, the hand wrap 10 may include a flexible mitten portion 12 having an interior side 14 and an exterior side 16. The mitten portion 12 may be made of a variety of flexible plastic or fabric materials, including, but not limited to, urethane foam and polyester fabric. The mitten portion 12 is configured to enclose at least the hand 4 of a patient in an open position, which advantageously reduces the possibility of numbness developing in the patient's hand 4 and fingers 1 during the surgical procedure. In examples, the interior side 14 of the mitten portion 12 adjacent to the palm of the hand 4 comprises an anti-slip material, such as styrene-butadiene rubber (SBR) bonded foam, rubber, or urethane foam. The hand 4 is secured within the mitten portion 12 by at least one closeable strap 20 (such as Velcro® straps) wrapped around the exterior side 16 of the mitten portion 12. For example, the straps 20 may be wrapped around the mitten portion 12 adjacent the patient's hand 4 and wrist 3. The straps 20 may be secured to the mitten portion 12 at one end or they may be free floating. The straps 20 are used to hold the hand 4 and wrist 3 firmly but not tightly within the mitten portion 12 to prevent any substantial movement of the hand 4 and wrist 3 in either rotation or translation.

Figure 3A:
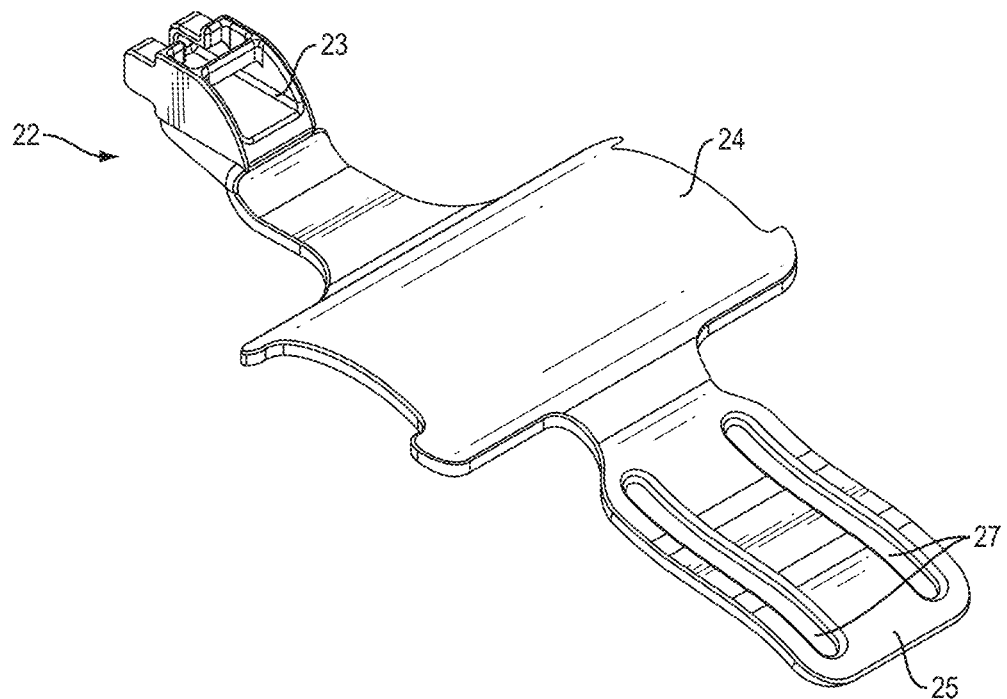
FIG. 3A illustrates an exemplary palm support plate of the hand wrap of this disclosure.
Figure 3B:
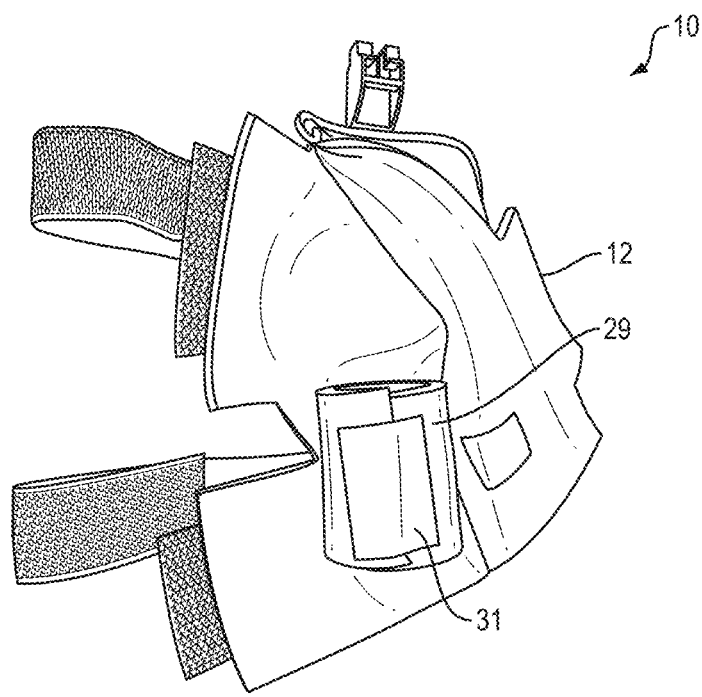
FIG. 3B illustrates an exemplary wrist support of the hand wrap of this disclosure.
Figure 4:
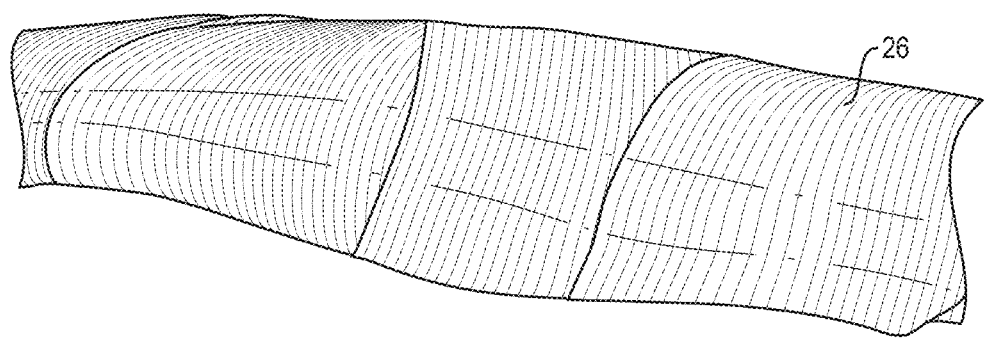
FIG. 4 shows an exemplary overwrapping of the hand wrap of this disclosure.

Once the hand 4 is secured within the mitten portion 12, the mitten portion 12 may be attached to an anatomically-shaped plate 22, shown in more detail to FIG. 3A. The plate 22 is configured to support the palm of the hand 4 in the open position. In examples, the plate 22 is comprised of a material which has adequate strength and resistance to sterilization using radiation, such as polycarbonate plate. Notably, the plate 22 can take a variety of sizes and shapes as long as it is configured to support the palm in the open position. In the example of FIG. 3A, the plate has a distal portion 23 configured to attach to a limb positioning device. The plate 22 also includes a center portion 24 which is curve-shaped to support the fingers 1 of the hand 4. Finally, the plate 22 includes a proximal portion 25. The proximal portion 25 may include one or more slots 27 through which the straps 20 may be passed to attach the mitten portion 12 to the plate 22 near the patient's wrist 3. In order to reduce slippage and pressure on the ulnar and radial sides of the wrist, which may lead to nerve injury, the hand wrap 10 may be provided with additional padding 29 within the mitten portion 12 for wrapping around the wrist of the patient, as shown in FIG. 3B. In examples, the padding may be a foam padding, and may be secured to the wrist by a strap 31 wrapped around the wrist. A thickness of the padding 29 is selected to be greater than a thickness of the mitten portion 12. Finally, the hand wrap 10 is overwrapped with an elastic bandage 26, as shown in FIG. 4. It is also contemplated by this disclosure that the hand 4 of the patient could be secured to the plate 22 without the use of the mitten portion 12.

Figure 5A:
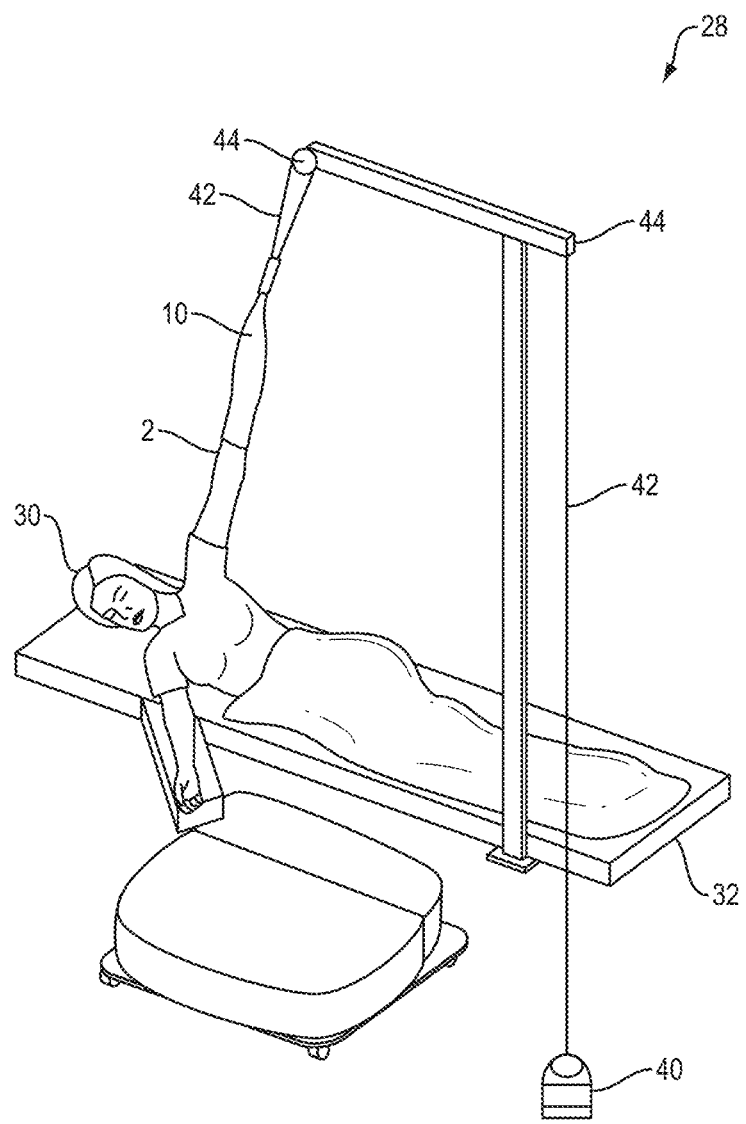
FIG. 5A is a schematic illustration of a limb positioning device for applying traction to the hand wrap of this disclosure.

Turning now to FIG. 5A, a limb positioning device 28 is illustrated, the component parts of which are described in more detail below. In FIG. 5A, a patient 30 is shown lying on a standard operating table 32 and prepared for a surgical operation. The forearm of the arm 2 to be operated upon is encased within the hand wrap 10 of this disclosure. The distal end of the hand wrap 10 is then attached to weights 40 via a series of ropes 42 and pulleys 44 on the limb positioning device 28. Advantageously, when traction is applied to the hand wrap 10 by the limb positioning device 28, the shape of the plate 22, the construction of the mitten portion 12, and the straps 20 combine to allow low-contact pressure across the hand 4 and the wrist 3 of the patient 30. In examples, various components of the limb positioning device may contain telescoping or other features for lengthening or shortening the components, and/or height adjusting features for raising or lowering the components.

Figure 5B:
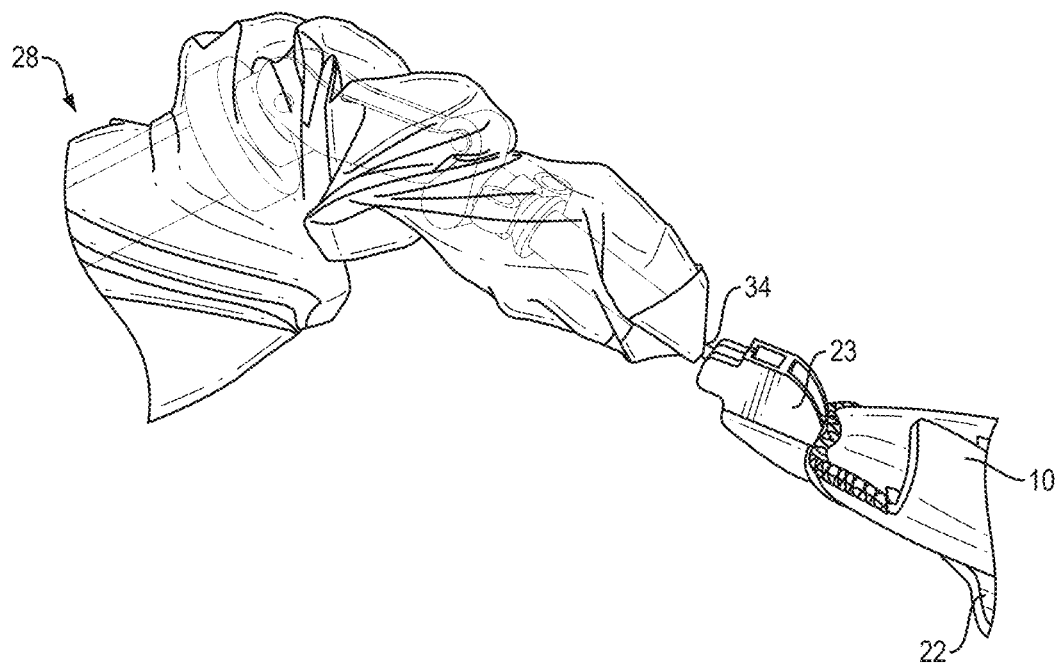
FIGS. 5B-E show an exemplary sterile connector and drape for connecting the hand wrap of this disclosure to the limb positioning device of FIG. 5A.
Figure 5C:
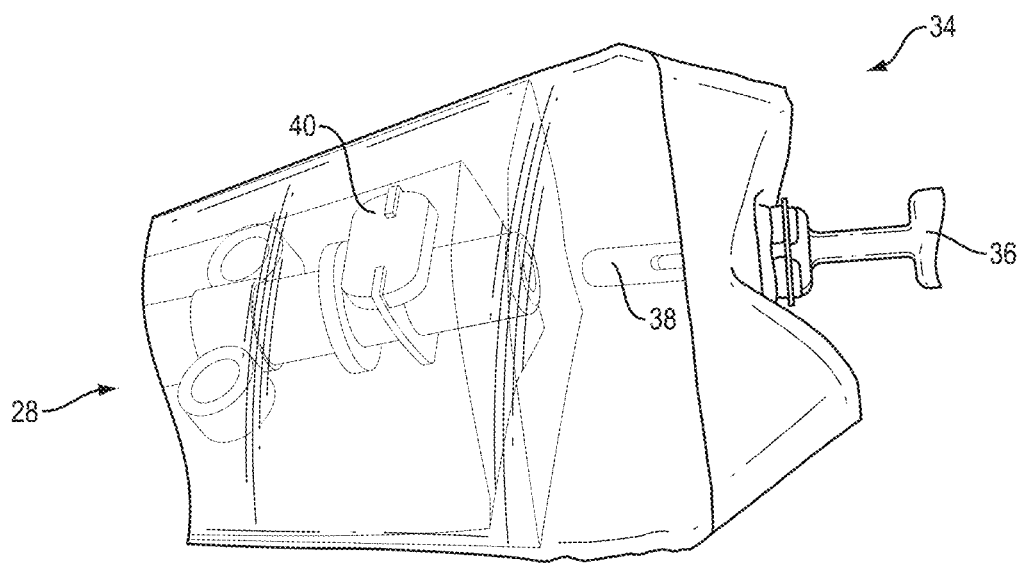

As shown in FIG. 5B, once the hand wrap 10 has been secured to the plate 22. The distal portion 23 of the plate 22 is connected to the limb positioning device 28 by means of an exemplary sterile connector 34 of this disclosure, shown in more detail in FIG. 5C. The sterile connector 34 may be made of polymers, metals or other suitable materials and is intended to be disposed of after use. As shown in FIG. 5C, the sterile connector 34 has a T-fitting 36 at its distal end and a keyed shaft 38 at its proximal end. The T-fitting 36 is configured to couple to the distal portion 23 of the plate 22 of the limb positioning device 28. The shaft 38 is configured to mate with a receiver 40 permanently attached to the distal end of the limb positioning device 28, as shown in FIG. 5D.

Figure 5D:
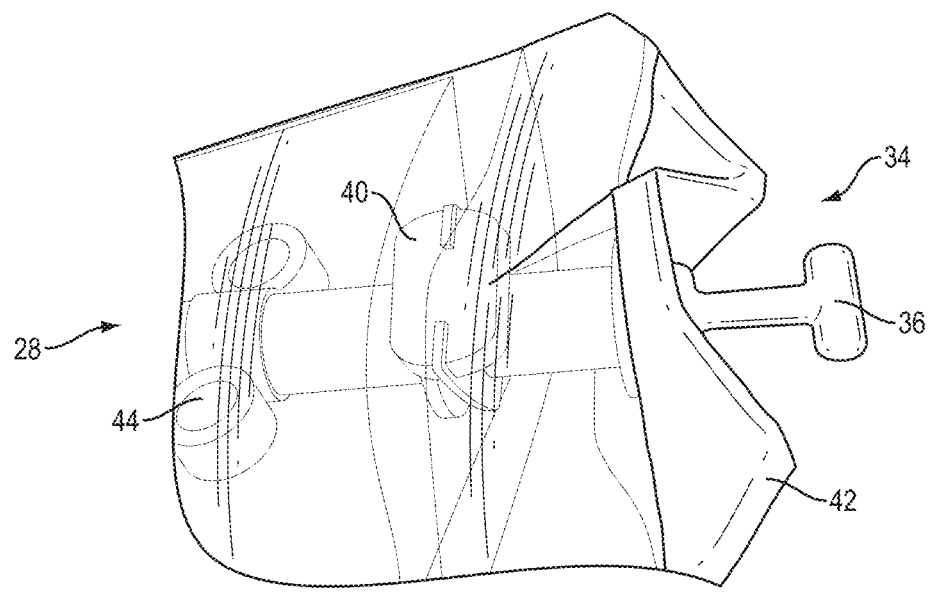
Figure 5E:
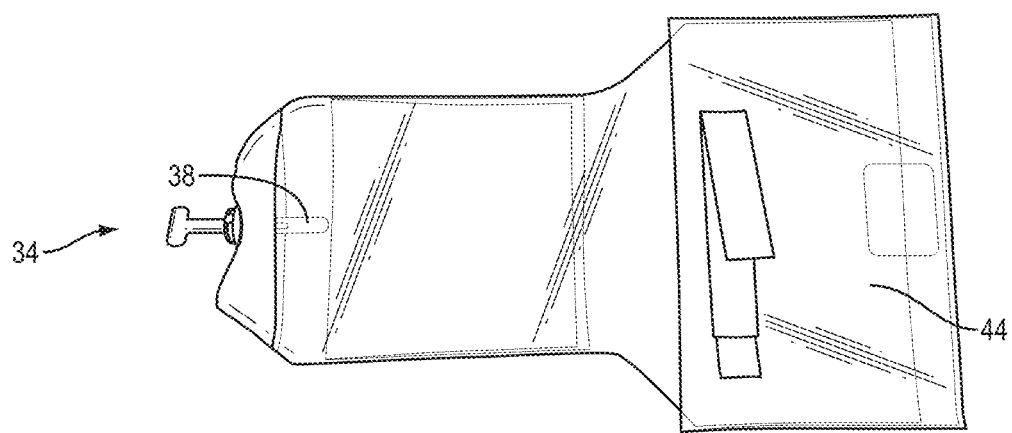

Also shown in FIG. 5D, attached to the sterile connector 34 is a flexible dam portion 42 of a sterile drape or covering 44. In examples, the proximal end of the covering 44 is open such that the covering 44 is configured to cover at least a portion of the limb positioning device 28. The covering 44 may be fabricated from a variety of different materials that may be sterilized and which are preferably latex-fee, such as polyethylene plastics. In examples, the covering 44 may be formed from a pre-formed tubular sheet of the plastic material or from plural sheets of plastic material formed into a tube with longitudinal seams. It will be appreciated that the dimensions and configuration of the covering 44 will vary depending upon the type and structure of the limb positioning device or other equipment that the covering 44 is designed to cover. The dam portion 42 is attached to the covering 44 in an appropriate manner such as sonic welding or adhesives. The dam portion 42 may be fabricated from any number of flexible, non-slip materials, such as rubber. In examples, the sterile connector 34 is held in the dam portion 42 in an interference fit due to the elastic nature of the rubber. As shown in FIG. 5E, in use, the covering 44 may be folded in telescopic fashion to allow for visualization of the shaft 38 of the sterile connector 34 for easing insertion into the receiver 40 of the limb positioning device 28.

In other examples, not shown, the shape of the T-fitting 36 and the shaft 38 could be changed to suit different applications. For example, the shaft 38 could be reconfigured to make it symmetrical to the T-fitting 36. In other examples, the sterile connector 34 could be clamped or glued in place, or held by a fastening ring. In addition, the dam portion 42 could be eliminated, allowing the covering 44 to be directly attached to the sterile connector 34. Advantageously, the sterile connector 34 of this disclosure allows for a sterile operator to attach the sterile hand wrap 10 to the limb positioning device 28 in the sterile field without the need for a non-sterile operator. This in turn allows for faster turnover between procedures by eliminating the need for re-usable (i.e., autoclaveabie) interfaces.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

What is claimed is:

1. A surgical hand wrap for attaching a patient's arm to a limb positioning device, the surgical hand wrap comprising:
   a flexible mitten portion having an interior side defining an inner portion and an exterior side, the flexible mitten portion configured to enclose at least a hand of the patient in an open position within the inner portion;
   an anatomically-shaped plate having a proximal portion and a distal portion, the anatomically-shaped plate coupled to the exterior side and exposed to an exterior of the flexible mitten portion, the anatomically-shaped plate configured for supporting a palm of the hand in the open position; and
   wherein the anatomically-shaped plate comprises a curved center portion extending between the proximal and distal portions, the curved center portion configured for supporting a plurality of fingers of the hand and the palm of the hand in the open position;
   at least one closeable strap for wrapping around the exterior side of the flexible mitten portion;
   wherein the distal portion of the anatomically-shaped plate is configured to attach to a T-fitting of a sterile connector of the limb positioning device; and
   wherein, when traction is applied to the patient's arm, the anatomically-shaped plate, the flexible mitten portion, and the at least one strap combine to allow low-contact pressure across the hand of the patient.

2. The surgical hand wrap of claim 1, wherein the flexible mitten portion is comprised of at least one of urethane foam and polyester fabric.

3. The surgical hand wrap of claim 1, wherein the interior side of the flexible mitten portion comprises an anti-slip material.

4. The surgical hand wrap of claim 3, wherein the anti-slip material is one of SBR bonded foam, rubber, and urethane foam.

5. The surgical hand wrap of claim 1, wherein an end of the at least one strap is attached to the flexible mitten portion.

6. The surgical hand wrap of claim 1, wherein the at least one strap is free-floating.

7. The surgical hand wrap of claim 1, wherein the at least one strap is secured to the anatomically-shaped plate.

8. The surgical hand wrap of claim 1, wherein the surgical hand wrap is enclosed within a bandage.

9. The surgical hand wrap of claim 1, wherein the anatomically-shaped plate is comprised of polycarbonate.

10. The surgical hand wrap of claim 1, wherein the proximal portion of the anatomically-shaped plate is configured to be secured to a wrist of the patient and the distal portion of the anatomically-shaped plate has a length selected to extend distally of a plurality of finger tips of the patient.

11. The surgical hand wrap of claim 1, wherein the proximal portion of the anatomically-shaped plate comprises at least one slot configured for the passage of the at least one strap.

12. The surgical hand wrap of claim 1, further comprising a padding disposed within the flexible mitten portion for securing about a wrist of the patient, a thickness of the padding selected to be greater than a thickness of the flexible mitten portion.

* * * * *